United States Patent [19]

Barrett et al.

[11] 4,395,075

[45] Jul. 26, 1983

[54] MISALIGNMENT SYSTEM FOR A MICROTOME

[75] Inventors: Lawrence R. Barrett, Washington; Allan J. Weiner, Weston, both of Conn.

[73] Assignee: E. I. Du Pont de Nemours & Co., Wilmington, Del.

[21] Appl. No.: 361,262

[22] Filed: Mar. 24, 1982

[51] Int. Cl.³ .................... F16C 32/02; G01N 1/06
[52] U.S. Cl. ........................... 308/2 R; 83/915.5
[58] Field of Search ............ 308/2 R, 2 A; 83/915.5

[56] References Cited

U.S. PATENT DOCUMENTS

| | | | |
|---|---|---|---|
| 664,118 | 12/1900 | Becker . | |
| 1,529,834 | 3/1925 | Green . | |
| 1,638,747 | 9/1927 | Runge . | |
| 2,014,643 | 9/1935 | Bakker | 72/77 |
| 2,312,250 | 2/1943 | Jacobus | 308/2 |
| 2,375,322 | 5/1945 | Pierce | 308/2 R |
| 2,636,757 | 4/1953 | Bakane | 287/87 |
| 2,901,944 | 9/1959 | Sparer | 88/40 |
| 3,184,197 | 5/1965 | Aller | 248/204 |
| 3,214,224 | 10/1965 | Lash | 308/176 |
| 3,220,290 | 11/1965 | Shandon | 83/171 |
| 3,245,707 | 4/1966 | Cook et al. | 287/101 |
| 3,385,510 | 5/1968 | Hollander, Sr. | 230/117 |
| 3,601,234 | 8/1971 | Ingraham | 192/2 |
| 3,628,411 | 12/1971 | Shatzel | 83/414 |
| 3,746,129 | 8/1973 | Knapp et al. | 184/6.26 |
| 3,771,405 | 11/1973 | Blum | 83/714 |
| 3,828,571 | 8/1974 | Lechner | 62/320 |
| 3,828,641 | 8/1974 | Sitte | 83/703 |
| 3,926,085 | 12/1975 | Shatzel | 83/718 |
| 3,978,686 | 9/1976 | Lechner et al. | 62/514 R |
| 3,986,754 | 10/1976 | Torrant | 308/196 |
| 4,024,779 | 5/1977 | Taugner et al. | 83/165 |
| 4,054,999 | 10/1977 | Harbottle | 33/181 AT |
| 4,150,468 | 4/1979 | Harbottle | 29/148.4 |
| 4,150,593 | 4/1979 | Butler | 83/42 |
| 4,221,438 | 9/1980 | Sitte et al. | 308/2 R |
| 4,287,968 | 9/1981 | Stensson et al. | 188/74 |

FOREIGN PATENT DOCUMENTS

| | | |
|---|---|---|
| 238963 | 3/1965 | Austria . |
| 398186 | 5/1909 | France . |
| 921405 | 3/1963 | United Kingdom . |
| 1352683 | 8/1974 | United Kingdom . |

*Primary Examiner*—Stuart S. Levy
*Assistant Examiner*—Thomas R. Hannon

[57] ABSTRACT

A misalignment pivot system for permitting pivotal movement of a main pivot socket in a direction along an axis Q-Q′ connecting a pair of main pivot balls includes a pair of misalignment pivot balls one of which is captured between a fixed socket and a V-groove. The misalignment pivot system permits pivotal movement of the main pivot socket without the imposition of a restoring force.

9 Claims, 4 Drawing Figures

4,395,075

MISALIGNMENT SYSTEM FOR A MICROTOME

BACKGROUND OF THE INVENTION

This invention relates to a pivot system for a microtome and, in particular, to a supplementary misalignment pivot arrangement for accommodating misalignment of elements in the main pivot system.

A microtome is a device adapted to provide extremely thin slices of a material for microscopic examination. Typically, the material to be sliced is mounted to the forward end of an articulable specimen holding arm which is itself pivotally mounted at its opposite end within a yoke. The yoke is itself pivotally mounted to the microtome frame and connected to an advance member, as a lead screw. In operation the specimen is drawn downwardly over the edge of a knife thereby slicing an extremely thin slice of specimen. In most instances, the slice is collected on the surface of a liquid reservoir. As the yoke is advanced the holding arm articulates thus permitting the specimen to be raised above the cutting edge of the knife in anticipation of the next downward cutting stroke.

In order to consistently and repeatably provide slices of the thicknesses required for the purpose under discussion extremely precise pivoting motion between all relatively movable members is an absolute requirement. Ball pivot assemblies are usually utilized to define the bearing surfaces for the pivotal movements above discussed. However, when ball pivots are used, there is a tendency for misalignments between the bearing balls and their associated sockets. Accordingly, when balls are used to define the surfaces on which the pivoting movement between the members occurs, some arrangement must be provided whereby the exact distances between the pivot balls and their corresponding sockets are maintained.

One method known in the art of achieving such exact matching distances between the pivot balls and their sockets is shown in Austrian Pat. No. 238,963. In this patent both of the pivot balls are fixed to one of two relatively pivotal members. However, each of these balls is supported in the other of the relatively pivotably members in a different manner. One of the balls is supported in a socket secured in a fixed location to the second member. The second of the balls is received in a substantially V-shaped groove provided in the second member. The corresponding ball may occupy any position within the groove thereby assuring exact matching of the distance between the balls and the distance between their corresponding support surfaces.

U.S. Pat. No. 4,221,438 (Sitte et al.) discloses an alternative technique. In one embodiment of the device shown in this patent one of the balls is introduced into a socket containing molten cement and permitted to situate itself such that when the cement sets up there is an exact matching of the distance between the balls and the sockets. In a second embodiment of the device shown in this patent one of the sockets is fixed to one of the members while the other of the bearing sockets is mounted on a leaf spring for flexural movement with respect to that member. In this manner deviations in the distances between the balls and the sockets may be accommodated so that exact matching of the bearing elements may be facilitated. However, the flexing of the leaf spring to accommodate misalignments between the sockets and balls results in the generation of a restoring force which is imposed on the system. This restoring force, acting in a direction parallel to the axis of the balls, may disrupt the precise slicing of sections of the required thickness.

Accordingly, it is believed advantageous to provide a misalignment system to support relatively pivotal members within a microtome so that perceived disadvantages attendant upon the use of flexural members does not occur.

SUMMARY OF THE INVENTION

This invention relates to a misalignment pivot system for a microtome, and particularly for an ultramicrotome in which a pair of main pivot balls is secured to a first member and corresponding main pivot sockets are provided for mounting onto a second member relatively pivotal with respect to the first member. One of the main pivot sockets is itself pivotal with respect to the second member on the supplemental misalignment pivot system. The misalignment pivot system includes a fixed socket and a groove formed on either of the main pivot socket or the first member and a pair of fixed sockets on the other of the main pivot socket or the first member. Corresponding fixed sockets and the socket and groove capture misalignment pivot balls on which pivotal movement of the main pivot socket with respect to the first member may occur. Thus, misalignments along the axis of the main pivot balls may be accommodated without the generation of a restoring force which may disrupt precise slicing of the specimen.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
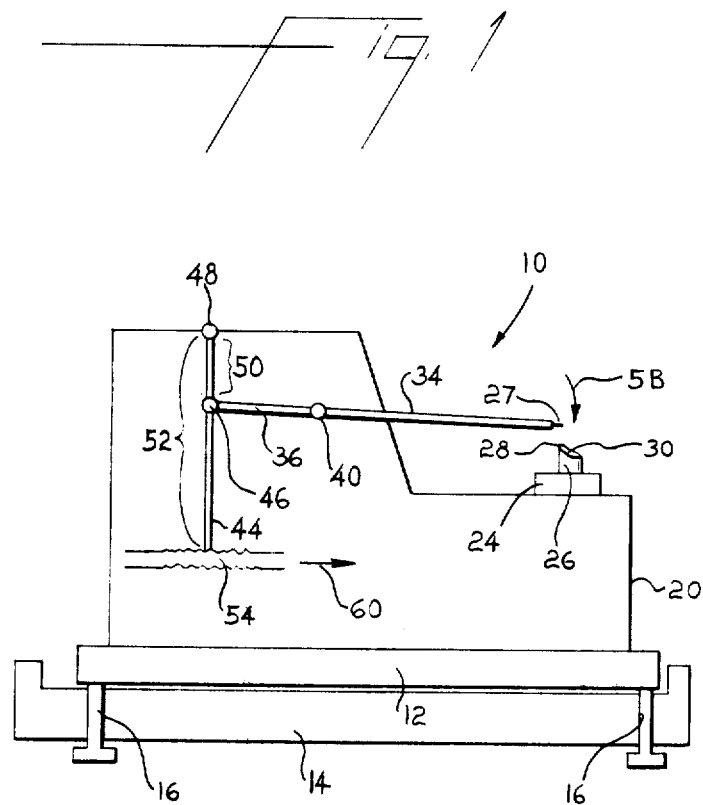
FIG. 1 is a highly stylized pictorial representation of a microtome with which the misalignment pivot system of the present invention finds particular utility.

Throughout the following description similar reference numerals refer to similar elements in all figures of the drawings.

With reference to FIG. 1 shown is a highly stylized pictorial representation of a microtome generally indicated by reference numeral 10. Although the misalignment pivot system in accordance with this invention may be used with any microtome apparatus, it is believed to have particular utility when used with an ultramicrotome. An ultramicrotome is a device adapted to produce specimen slices with thicknesses on the order of nanometers.

The microtome 10 includes a frame 12 mounted within an outer casing 14 by any suitable means of attachment, such as the shock mounts 16. The frame 12 is a relatively massive member which supports a microtome superstructure indicated by reference character 20 on three contact pads (not shown). As is discussed herein, the superstructure 20 is that portion of the microtome which supports those components important to the cutting process (e.g., the knife and specimen holding arm). By mounting the superstructure 20 with a three-point contact the frame 12 is allowed to flex without affecting the superstructure 20 and the cutting components thereon, thereby elminating chatter, a source of imprecision in slice thickness.

A stage 24 is adjustably mounted on the superstructure 20 by any suitable attachment mechanism. The stage 24 carries a suitable specimen cutting element, such as the knife 26. The knife 26 serves to produce a series of thin slices of a specimen 27 as the specimen 27 is drawn over the cutting edge 28 of the knife. In practice, the slices of the specimen are most commonly collected on the surface of a liquid contained in a boat 30 formed in the knife 24 forwardly of the cutting edge 28.

The specimen 27 from which slices are cut is supported at the outboard end of a specimen holding arm 34. The specimen holding arm 34 is pivotally mounted for articulated movement with respect to a housing member 36 on a retract pivot assembly generally indicated by reference character 40. The housing 35 is itself pivotally mounted with respect to a yoke 44 on a cutting pivot assembly 46. The yoke 44 is pivotally mounted with respect to the superstructure 20 on an advance pivot assembly 48. The advance pivot assembly 48 is mounted a predetermined distance 50 (exaggerated for clarity of illustration in FIG. 1) above the cutting pivot assembly 46 for purposes understood by those in the art. The free end of the yoke 44 is secured a predetermined distance 52 below the pivot assembly to an advance mechanism, such as a lead screw 54. The advance mechanism is suitably supported for movement with respect to the superstructure 20.

The operation of the microtome 10 shown in FIG. 1 is readily understandable from the foregoing by those skilled in the art. The specimen holding arm 34 and the housing 36 pivot with respect to the yoke 44 on the cutting pivot assembly 46 to move the specimen 27 in the direction of the arrow 58 over the cutting edge 28 of the knife 26. The specimen holding arm 34 articulates on the retract pivot assembly 40 to permit the specimen 27 to be returned to a position above the cutting edge 28 preparatory to the next cut. The yoke 44 is pivoted with respect to the superstructure 20 on the advance pivot assembly 48 to thereby advance the specimen holding arm 34 in the direction of the arrow 60 prior to the next cut of the specimen 27. The magnitude of the advance of the specimen 27 in the direction 60 with respect to the superstructure 20 is functionally related to the ratio of the distances 50 and 52. It is to be understood that suitable cams and actuators for the motions discussed are provided, but that these elements are omitted from the Figures for clarity of illutration.

Figure 2:
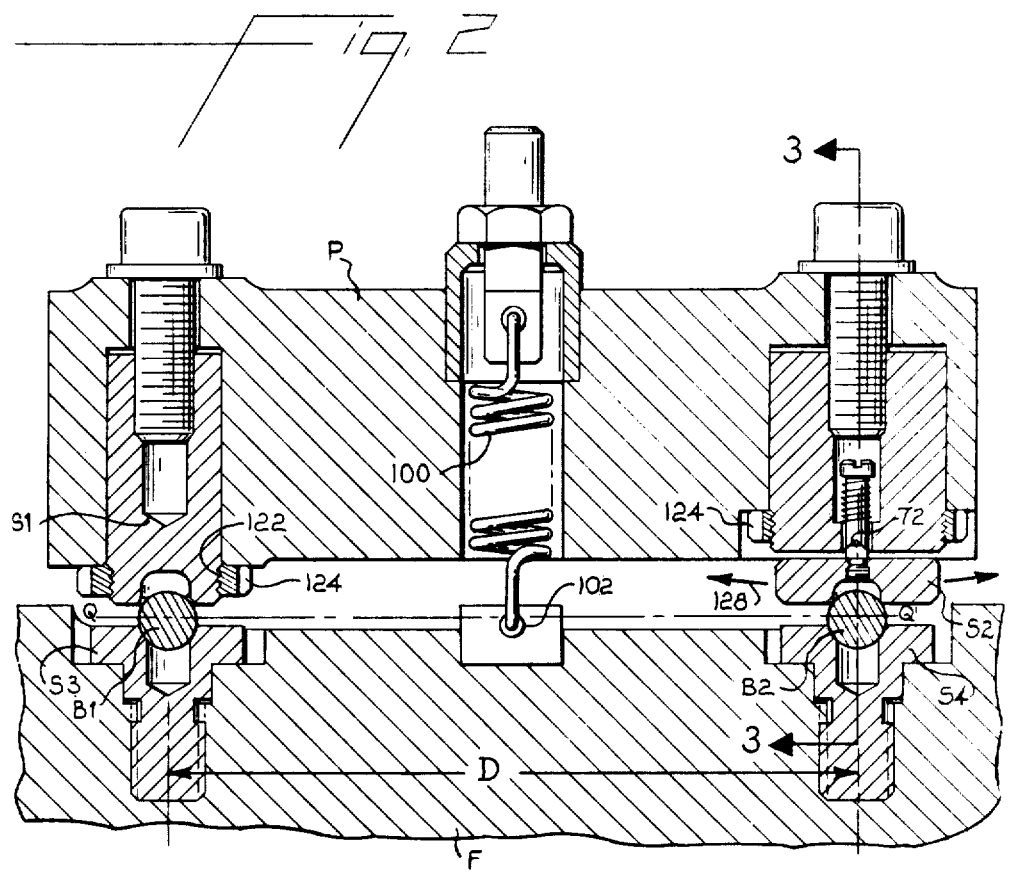
FIG. 2 is a front elevational view of a generalized misalignment pivot system embodying the teachings of the present invention for use between two relatively pivotable members of a microtome.
Figures 3, 4:
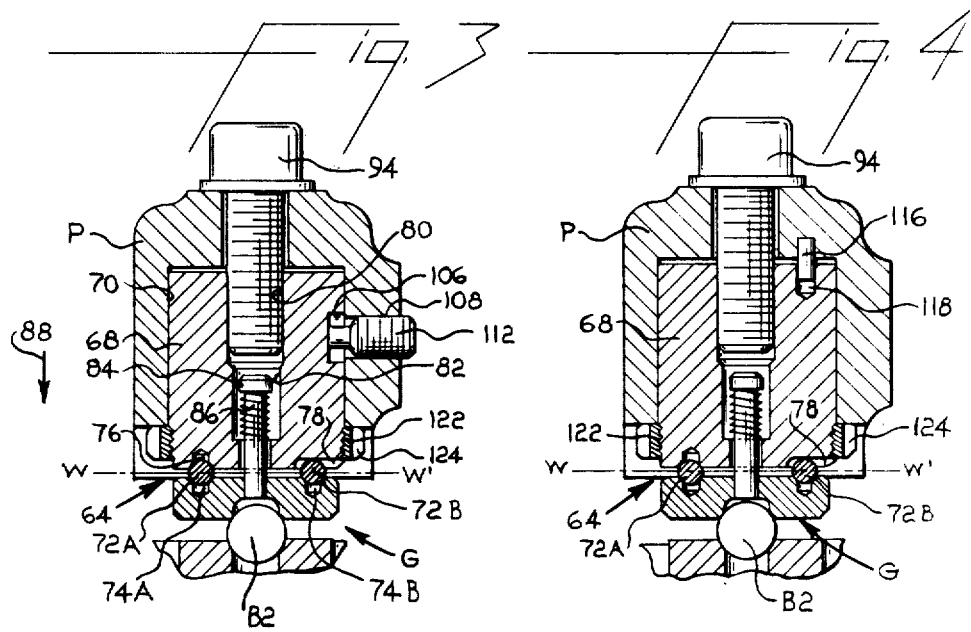
FIG. 3 is a side sectional view taken along section lines 3—3 in FIG. 2.
FIG. 4 is a view similar to FIG. 3 illustrating an alternate arrangement for locating the misalignment pivot system.

With reference to FIGS. 2 and 3, shown is a front section and a side section view of a generalized pivot assembly indicated by the reference character G with which may be used a misalignment pivot system in accordance with this invention and generally indicated by the reference character 64. As seen in FIGS. 2 and 3, a first member P is mounted for pivotal movement on a pair of mean pivot balls B1 and B2 with respect to a second relatively fixed member F.

The main pivot balls B1 and B2 are spaced a predetermined distance D apart as measured in a direction parallel to the axis Q-Q' extending through the centers of the balls. Each of the main pivot balls B1 and B2 is respectively received between corresponding pairs of main sockets S1, S3 and S2, S4.

Preferably, the socket S1 is secured to the first, pivotable, member P while the sockets S3 and S4 are mounted to the second, relatively fixed, member F. The socket S2 is mounted by the supplemental misalignment pivot system 64 for pivotal movement with respect to the first member P. In practice, it is preferred that the main balls B be secured, as by glue or the like, into the main sockets which are carried on the member with respect to which pivotal motion is to occur. For example, if the first member P is pivotally movable with respect to the second member F, the balls B are glued or otherwise secured into the sockets S3 and S4. The movable socket (S2 in FIGS. 2 and 3) would therefore be mounted for pivotal movement on the supplemental misalignment pivot system 64 with respect to the pivoting member, i.e., the first member P in the example. It should be understood, however, that the mounting location of the movable socket S2 and its corresponding socket S4 may be reversed. That is, the socket S2 may be mounted on the supplementary pivot system 64 for movement with respect to the relatively fixed members F, while the socket S4 is secured to the pivotable member P.

The misalignment pivot system 64 includes a pivot support member 68 mounted in a recess 70 provided in the pivotable member P if the socket S2 is to be pivotable with respect to the member P. Of course, if the socket S2 is to pivot with respect to the member F, that member would receive the support 68. The misalignment pivot system 64 further includes first and second misalignment pivot balls 72A and 72B respectively. The pivot balls 72A and 72B are disposed intermediate fixed sockets 74A and 74B (preferably formed in the pivot socket S2) and a corresponding fixed socket 76 and a V-groove 78 (preferably formed in the pivot support member 68). Of course, the pivot support member 68 may be arranged to carry only fixed sockets (i.e., a pair of sockets similar to the sockets 74) while the main pivot socket S2 may carry both a fixed socket similar to the socket 76) and a V-groove (similar to the groove 78). Any adjustments in the direction along the axis W-W' between the misalignment pivot balls 72A and 72B is accommodated by displacement of the pivot ball 72B to an appropriate position in the groove 78. The axis W-W' extends substantially perpendicular to the axis Q-Q' of the main pivot system.

The pivot support member 68 has a central bore 80 extending therethrough which is counterbored, as at 82, to accommodate a threaded screw 84. The screw 84 captures a spring 86 which acts in a direction 88 between the underside of the head of the screw 84 and the bottom of the shoulder formed by the counterbore 82. During assembly the balls 72A and 72B are glued or otherwise secured to the fixed sockets 74A and 74B, respectively. The screw 84 is threaded into the main pivot socket S2 to thereby hold the components of the misalignment pivot system in place while the support 68 is inserted into the recess 70. The support 68 is held in place with respect to the member P by a bolt 94. A holding spring 100 is provided between the members F and P. It should be noted that the point 102 at which the spring 100 bears against the member F lies on the axis Q-Q'. Thus, the force exerted by the spring 100 is the same through the full pivotal movement of the member P.

The pivot support 68 includes a recess 106 which registers with a bore 108 provided in the member P. A set screw 112, when inserted through the bore 108 and into the recess 106, serves to dispose the axis W-W' extending through the misalignment pivot balls 72 in a substantially perpendicular relationship to the axis Q-Q' extending through the main pivot balls B1 and B2.

As seen in FIG. 4, the substantially perpendicular relationship between the axes of the misalignment pivot balls 72 and the main pivot balls may be achieved in an alternate manner. A pin 116 is press fit or otherwise secured into some portion of the member P. The pivot support 68 is provided with a bore 118 located at a predetermined location with respect to the axis W-W' such that when the pin 116 is received within the bore 118 the axis W-W' is substantially perpendicular to the axis Q-Q'.

The socket S1 and the support member 68 for the socket S2 may be provided with an adjustment assembly, such as exterior threads 122 and a lock nut 124, whereby the position of the centers of each of the main pivot balls B1 and B2 may be varied with respect to a reference datum. In the case of the main pivot socket S2, the threads 122 and lock nut 124 may be provided on the support member 68. In the context of the microtome shown schematically in FIG. 1, the adjustment feature just discussed permits the setting of the offset distance 50 between axis Q-Q' through the main pivot balls provided in the advance pivot assembly 48 with respect to the axis W-W' extending through the supplemental pivot balls provided in the advance pivot assembly.

In operation, any adjustment of one of the main pivot sockets or one of the main pivot balls with respect to the first member P and/or the second member F in the direction of the axis Q-Q' to match the exact separation between the main pivot sockets or the main pivot balls is accommodated by deflection of the pivoting socket S2 in the directions of arrows 128 on the bearing surfaces provided by the misalignment pivot balls 72. By the pivoting movement of the main pivot socket S2 in the direction of the arrows 128 exact matching of the distances between the main pivot balls and their associated sockets can be accommodated without the imposition of a restoring force generated in flexural pivot systems.

Having above described the present invention those skilled in the art will realize that this invention provides a system whereby exact matching of the distances between the centers of the main pivot balls and their associated sockets is accommodated without flexure of any member and the generation of a concomitant restorative force. This restorative force is believed to engender inaccuracies in the uniformity of slices produced and the elimination of the restorative force is therefore believed to be advantageous. It should also be appreciated that utilization of the misalignment pivot system hereinabove disclosed provides a structure whereby the main pivot socket may displace in one plane (i.e., the plane of FIG. 2) while remaining stiff in a transverse plane.

The misalignment pivot system of the present invention may be used in any of the pivot assemblies in a microtome wherein relative pivoting motion between members is desired. Thus, the misalignment pivot system may be used in the retract pivot assembly, in the cutting pivot assembly, in the advance pivot assembly and/or wherever else relative pivotal motion between two members occurs. As examples, when used in the retract pivot assembly 40, the specimen holding arm 34 and the housing 36 may be respectively construed as the first member P and the second member F. In the instance of the cutting pivot assembly 46, the housing 36 and the yoke 44 may be respectively construed as the first member P and the second member F. In the advance pivot assembly 48, the yoke 44 and the superstructure 20 may be construed as the first member P and the second member F. In the case of the advance pivot assembly 48, the ability to adjust the main pivot balls relative to a reference datum (the axis W-W' of the misalignment pivot balls) through the agency of the threads 122 and lock nut 124 finds especial utility in assisting to define the predetermined distance 50 between the cutting pivot assembly 46 and the advance pivot assembly 48.

Those skilled in the art having teachings in the invention as hereinabove set forth may effect numerous modifications thereto. These modifications are to be construed as lying within the scope of the instant invention as defined in the appended claims.

What is claimed is:

1. In a microtome of the type having a first member pivotally movable with respect to a second member on a pair of main pivot balls captured between fixed sockets provided on one of the members and a fixed and a movable socket provided on the other of the members, the improvement which comprises:

a misalignment pivot system for permitting movement without the generation of a restoring force of the movable socket in the direction of an axis (Q-Q') connecting the centerlines of the balls to match the exact separation between the main pivot balls, the misalignment pivot system itself comprising a socket and a groove formed on either the movable socket or on one of the members and a pair of fixed sockets confrontationally provided on the other of the movable socket or the one of the members, a first misalignment pivot ball captured between a pair of fixed sockets and a second misalignment pivot ball captured between the fixed socket and the groove, the axis (W-W') between the centers of the misalignment pivot balls being substantially perpendicular to the axis (Q-Q') connecting the centerlines of the main pivot balls.

2. In a microtome of the type having a first member pivotally movable with respect to a second member on a pair of main pivot balls captured between fixed sockets provided on the second member and a fixed and a movable socket provided on the first member, the improvement which comprises:

a misalignment pivot system for permitting movement without the generation of a restoring force of the movable socket in the direction of an axis (Q-Q') connecting the centerlines of the balls to match the exact separation between the main pivot balls, the misalignment pivot system itself comprising a socket and a groove formed on either the movable socket or the first member and a pair of fixed sockets confrontationally provided on the other of the movable socket or the first member, a first misalignment pivot ball captured between a pair of fixed sockets and a second misalignment pivot ball captured between the fixed socket and the groove, the axis (W-W') between the centers of the misalignment pivot balls being substantially perpendicular to the axis (Q-Q') connecting the centerlines of the main pivot balls.

3. Apparatus according to claim 2 wherein the first member is provided with a recess, a support member being receivable within the recess, the support member being provided with the pair of fixed sockets or the fixed socket and the groove, as the case may be, disposed in the confrontational relationship with the movable socket.

4. Apparatus according to claim 3 wherein the support member has a groove therein to receive a set screw to orient the axis (W-W') between the centers of the misalignment pivot balls substantially perpendicular to the axis (Q-Q') connecting the centers of the main pivot balls.

5. Apparatus according to claim 3 wherein the first member is provided with a pin and the support member has a bore therein, the pin and bore being arranged such that when the pin is received in the bore and axis (W-W') between the centers of the misalignment pivot balls is substantially perpendicular to the axis (Q-Q') connecting the centers of the main pivot balls.

6. In a microtome of the type having a first member pivotally movable with respect to a second member on a pair of main pivot balls captured between fixed sockets provided on the first member and a fixed and a movable socket provided on the second member, the improvement which comprises:
   a misalignment pivot system for permitting movement without the generation of a restoring force of the movable socket in the direction of an axis (Q-Q') connecting the centerlines of the balls to match the exact separation between the main pivot balls,
   the misalignment pivot system itself comprising a socket and a groove formed on either the movable socket or the second member and a pair of fixed sockets confrontationally provided on the other of the movable socket or the second member, a first misalignment pivot ball captured between a pair of fixed sockets and a second misalignment pivot ball captured between the fixed socket and the groove, the axis (W-W') between the centers of the misalignment pivot balls being substantially perpendicular to the axis (Q-Q') connecting the centerlines of the main pivot balls.

7. Apparatus according to claim 6 wherein the second member is provided with a recess, a support member being receivable within the recess, the support member being provided with the pair of fixed sockets or the fixed socket and the groove, as the case may be, disposed in the confrontational relationship with the movable socket.

8. Apparatus according to claim 7 wherein the support member has a groove therein to receive a set screw to orient the axis (W-W') between the centers of the misalignment pivot balls substantially perpendicular to the axis (Q-Q') connecting the centers of the main pivot balls.

9. Apparatus according to claim 7 wherein the second member is provided with a pin and the support member has a bore therein, the pin and bore being arranged such that when the pin is received in the bore the axis (W-W') between the centers of the misalignment pivot balls is substantially perpendicular to the axis (Q-Q') connecting the centers of the main pivot balls.

* * * * *